(12) United States Patent
Gottschalk-Gaudig et al.

(10) Patent No.: US 8,344,033 B2
(45) Date of Patent: *Jan. 1, 2013

(54) PARTICLE-STABILISED EMULSIONS

(75) Inventors: Torsten Gottschalk-Gaudig, Mehring (DE); Herbert Barthel, Emmertin (DE); Bernard Paul Binks, Walkington (GB); Tommy S. Horozov, Beverley (GB)

(73) Assignee: Wacker Chemie AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/932,563

(22) Filed: Feb. 28, 2011

(65) Prior Publication Data
US 2011/0178207 A1 Jul. 21, 2011

Related U.S. Application Data

(63) Continuation of application No. 10/599,026, filed as application No. PCT/EP2005/002887 on Mar. 17, 2005, now abandoned.

(30) Foreign Application Priority Data

Mar. 25, 2004 (DE) .......................... 10 2004 014 704

(51) Int. Cl.
| | |
|---|---|
| *B01F 3/08* | (2006.01) |
| *B01J 13/00* | (2006.01) |
| *C08L 63/00* | (2006.01) |
| *C08L 83/04* | (2006.01) |
| *C11D 10/00* | (2006.01) |
| *A61K 9/107* | (2006.01) |
| *A61K 8/06* | (2006.01) |
| *A61K 47/02* | (2006.01) |
| *C09D 5/02* | (2006.01) |
| *C09J 11/02* | (2006.01) |
| *C09K 3/10* | (2006.01) |
| *C08L 101/12* | (2006.01) |

(52) U.S. Cl. ............. 516/55; 516/22; 516/924; 516/23; 524/588; 523/466; 510/417; 514/938; 514/939

(58) Field of Classification Search .................... 516/54, 516/55, 22, 23, 924; 524/588; 523/466; 510/417; 514/938, 939
See application file for complete search history.

(56) References Cited

U.S. PATENT DOCUMENTS

| | | | |
|---|---|---|---|
| 5,643,555 A | 7/1997 | Collin et al. | |
| 5,686,054 A | 11/1997 | Barthel et al. | |
| 5,851,715 A | 12/1998 | Barthel et al. | |
| 6,709,662 B1 | 3/2004 | Gers-Barlag et al. | |
| 7,541,405 B2 * | 6/2009 | Gottschalk-Gaudig et al. ............. | 524/559 |
| 7,722,891 B2 * | 5/2010 | Barthel et al. ................ | 424/400 |
| 2003/0175221 A1 | 9/2003 | Gers-Barlag et al. | |
| 2003/0175317 A1 | 9/2003 | Barthel et al. | |
| 2004/0127580 A1 | 7/2004 | Baran, Jr. et al. | |
| 2004/0131527 A1 | 7/2004 | Gottschalk-Gaudig et al. | |
| 2005/0266055 A1 | 12/2005 | Stiller et al. | |
| 2007/0209552 A1 * | 9/2007 | Gottschalk-Gaudig .... | 106/287.1 |
| 2007/0281878 A1 | 12/2007 | Gottschalk-Gaudig et al. | |

FOREIGN PATENT DOCUMENTS

| | | |
|---|---|---|
| DE | 102 38 649 A1 | 3/2004 |
| EP | 0 987 008 A2 | 3/2000 |
| EP | 1240893 A1 | 9/2002 |
| EP | 1 433 749 A1 | 12/2003 |
| EP | 1526153 A1 | 4/2005 |
| JP | 06016008 A | 1/1994 |
| JP | 08169808 A | 7/1996 |
| JP | 2003311144 A | 5/2003 |
| JP | 2006515308 A | 5/2006 |

OTHER PUBLICATIONS

Derwent Abstract, week 200761, London: Derwent Publications Ltd., AN2004-238922, DE 102386439A, (Beiersdorft AG), abstract.
Derwent Abstract, week 201016, London: Derwent Publications Ltd., AN2005-758305, WO 2005092989 A1, (Wacker Chem AG), abstract.
Derwent Abstract, week 200780, London: Derwent Publications Ltd., AN 2000-273047, DE 19842787 A1, (Beiersdorf AG), abstract.
B.P. Binks et al., "Transitional Phase Inversion of Solid-Stabilized Emulsions Using Particle Mixtures", Langmuir, 2000, 16, 3748-3756 (Published on web Mar. 2000).
B.P. Binks and S.O. Lumsdon, "Effects of oil type and aqueous phase composition on oil-water mixtures containing particles of intermediate hydrophobicity", Phys. Chem. Chem. Phys., 2000, 2, 2959-2967 (Published on web Jun. 2000).
Derwent Abstract, week 200972, London: Derwent Publications Ltd., AN 2004-527025, EP 1433749 A1, (Wacker Chem. AG), abstract.
Derwent Abstract, week 200742, London: Derwent Publications Ltd., AN 2000-273054, EP 987008 A1, (Beiersdorf AG), abstract.
B.R. Midmore and T.M. Herrington, "Silica-stabilised multiple emulsions", Progr Colloid Polym Sci (1999) 112: 115-120 (Obtained online @ http://www.springerlink.com/content/y321qkn2f50rwaa9 (downloaded Mar. 25, 2010).
H. Barthel, "Surface interactions of dimethylsiloxy group-modified fumed silica", Colloids and Surfaces A: Physicochemical and Engineering Aspects 101 (1995) 217-226, Obtained online @ http://www.sciencedirect.com/science/journal/09277757, (Aug. 30, 1995).

(Continued)

*Primary Examiner* — Daniel S Metzmaier
(74) *Attorney, Agent, or Firm* — Brooks Kushman P.C.

(57) ABSTRACT

The invention relates to water-in-oil (W/O) or oil-in-water (O/W) emulsions containing an oil phase of at least one water-insoluble constituent; an aqueous phase; pyrogenic silica at the oil-water interface, the pyrogenic silica partially silylated such that non-silylated surface silanol groups remaining are between 95% and 5% of initial silanol groups, the equivalent of 1.7 to 0.1 surface SiOH groups per $nm^2$, a surface energy gamma-s-D of 30 to 80 $mJ/m^2$, and a specific BET surface area between 30 and 500 $m^2/g$; and optionally other substances, such as pigments or preservatives. The inventive emulsions have a mean particle size of the dispersed phase, of between 0.5 μm and 500 μm, and are of low viscosity.

8 Claims, 5 Drawing Sheets

OTHER PUBLICATIONS

English Abstract, corresponding to Lagaly et al., "Dispersions and Emulsions", Darmstadt 1997, ISBN 3-7985-1087-3, p. 1 to 4.

"Dispersions and Emulsions", Darmstadt 1997, ISBN 3-7985-1087-3, p. 1 to 4. Lagaly et al.

De Rooij, et al., "Steady Shear Viscosity of Weakly Aggregating Polystyrene Latex Dispersions", J. Chem. Phys., vol. 99, No. 11, Dec. 1, 1993, p. 9213-9223.

Papirer, et al., "Inverse Gaschromatography"—Characterisation of Polymers and Other Materials, 391 ACS Symposium Series, Chapter 18, pp. 248-261, ACS, Washington, DC (1989).

Sears et al., "Determination of Specific Surface Area of Colloidal Silica by Titration with Sodium Hydroxide", Anal. Chem. vol. 28, No. 12 (1950). 1981.

Washburn, E.W., "The Physical Review—The Dynamics of Capillary Flow", vol. 17, No. 3, Mar. 1921, pp. 273ff.

Schoelkopf, et al., "Measurement and network Modeling of Liquid Permeation into compacted Mineral Blocks", Journal of Colloid and Interface Science 227, pp. 119-131 (2000).

* cited by examiner

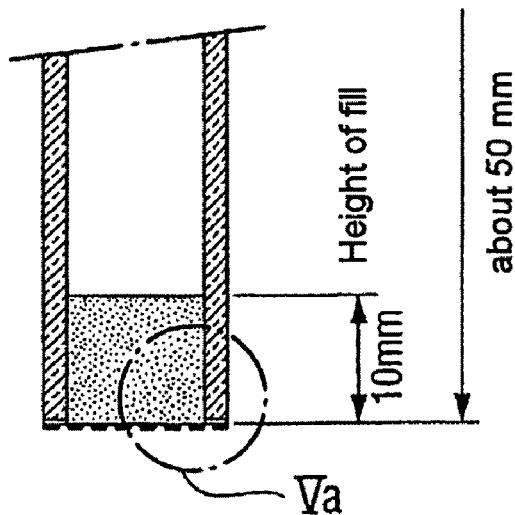
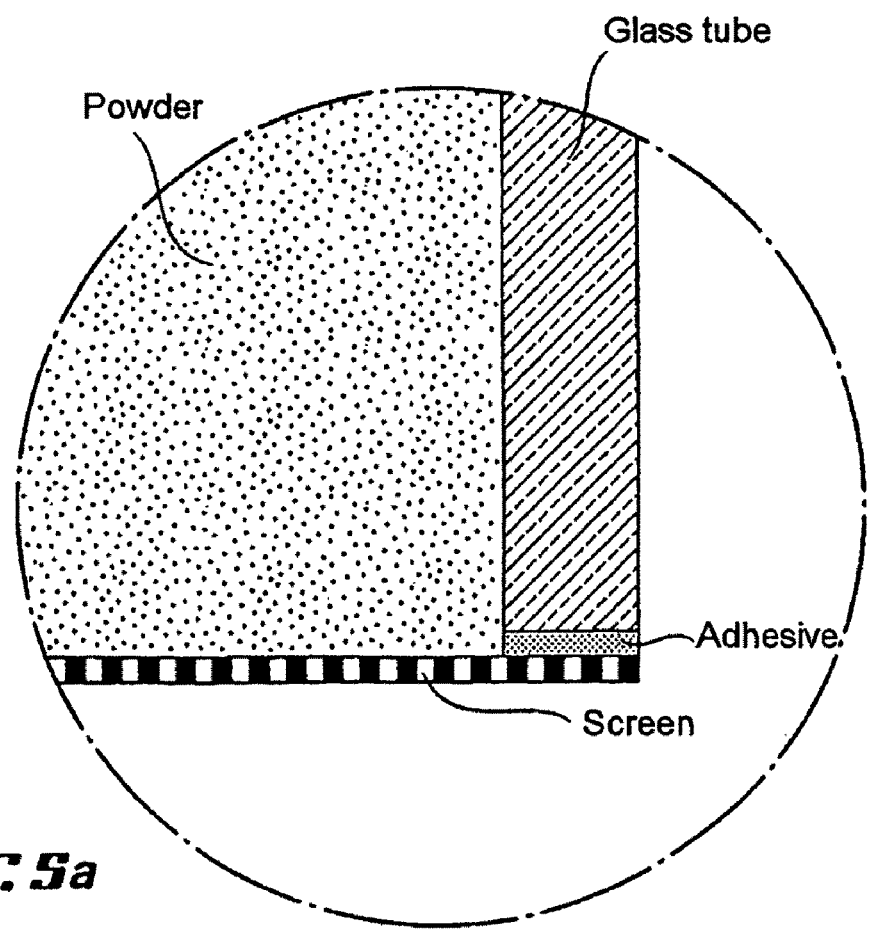

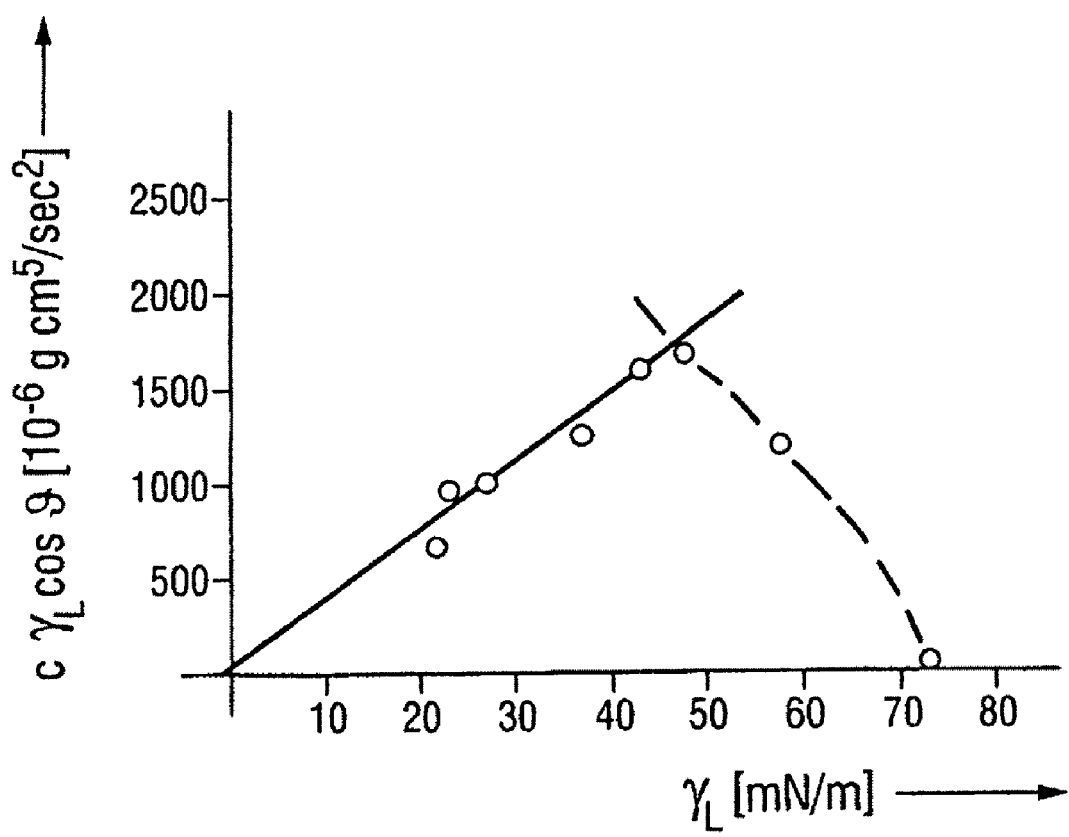

PARTICLE-STABILISED EMULSIONS

CROSS-REFERENCE TO RELATED APPLICATION

This application is a continuation of U.S. application Ser. No. 10/599,026, filed May 31, 2007 (now abandoned), which is the U.S. national phase of PCT Appln. No. PCT/EP2005/002887 filed Mar. 17, 2005, which claims priority to German application 10 2004 014 704.3 filed Mar. 25, 2004.

BACKGROUND OF THE INVENTION

1. Field of the Invention

The invention relates to emulsions of the water-in-oil (W/O) or oil-in-water (O/W) type and the preparation thereof.

2. Description of the Related Art

Emulsions, either as water-in-oil (W/O) or oil-in-water (O/W) dispersions, are widely used as an application form for coating materials, such as, for example, water-based paints and finishes, as adhesives and sealants, such as, for example, aqueous epoxy or polyurethane systems, as cosmetic formulations, as cleansing agents and disinfectants, in the food industry, for the surface modification of solid or liquid substrates or as reaction media in emulsion polymerization.

In general, the dispersing and stabilization of the disperse phase are effected with the aid of emulsifiers. Cationic, anionic, ampholytic and nonionic emulsifiers are used. Common to the emulsifiers is that they are surface-active substances. That is to say, they preferably accumulate at interfaces, such as, for example, liquid-liquid, liquid-solid or liquid-gas interfaces, and thus reduce the interfacial/surface energy. On application of the emulsion, however, the emulsifiers can also cover the surface of the substrate to be treated and thus greatly change the wetting properties of the surface. This can adversely affect, for example, the adhesion properties of a coating material or of an adhesive joint or seal. Furthermore, the recoatability may be adversely affected. In addition, emulsifiers based on organic molecules are potential hazardous substances when used in pharmaceutical or cosmetic formulations or in foods.

In 1907, Pickering described for the first time the preparation of emulsions which were stabilized only by addition of various solids, such as basic copper sulfates, basic iron sulfates or other metal salts. This type of emulsion is also referred to as a "Pickering emulsion". Basic investigations showed that a characteristic of Pickering emulsions is that solid particles are arranged at the interface between the two liquid phases and form a barrier there to the coalescence of the disperse phase.

Frequently, however, such solid-stabilized emulsions as described, for example, in EP 987008 have a high viscosity and/or a great tendency for separation, i.e. for creaming or sedimentation of the disperse phase.

SUMMARY OF THE INVENTION

It was an object of the invention to overcome the disadvantages of the prior art, in particular to provide low-viscosity and sedimentation-stable emulsions having a dispersed phase with a small particle diameter. These and other objects are achieved by employing as a dispersion stabilizer a pyrogenic silica which has been partially silylated, and has specific surface properties.

BRIEF DESCRIPTION OF THE DRAWINGS

FIGS. 5 and 5a illustrate one method of measuring the contact angle of a partly hydrophoticized filler against water.

FIG. 6 illustrates a Zisman plot for determining surface energy.

DETAILED DESCRIPTION OF THE PREFERRED EMBODIMENTS

Figure 1:
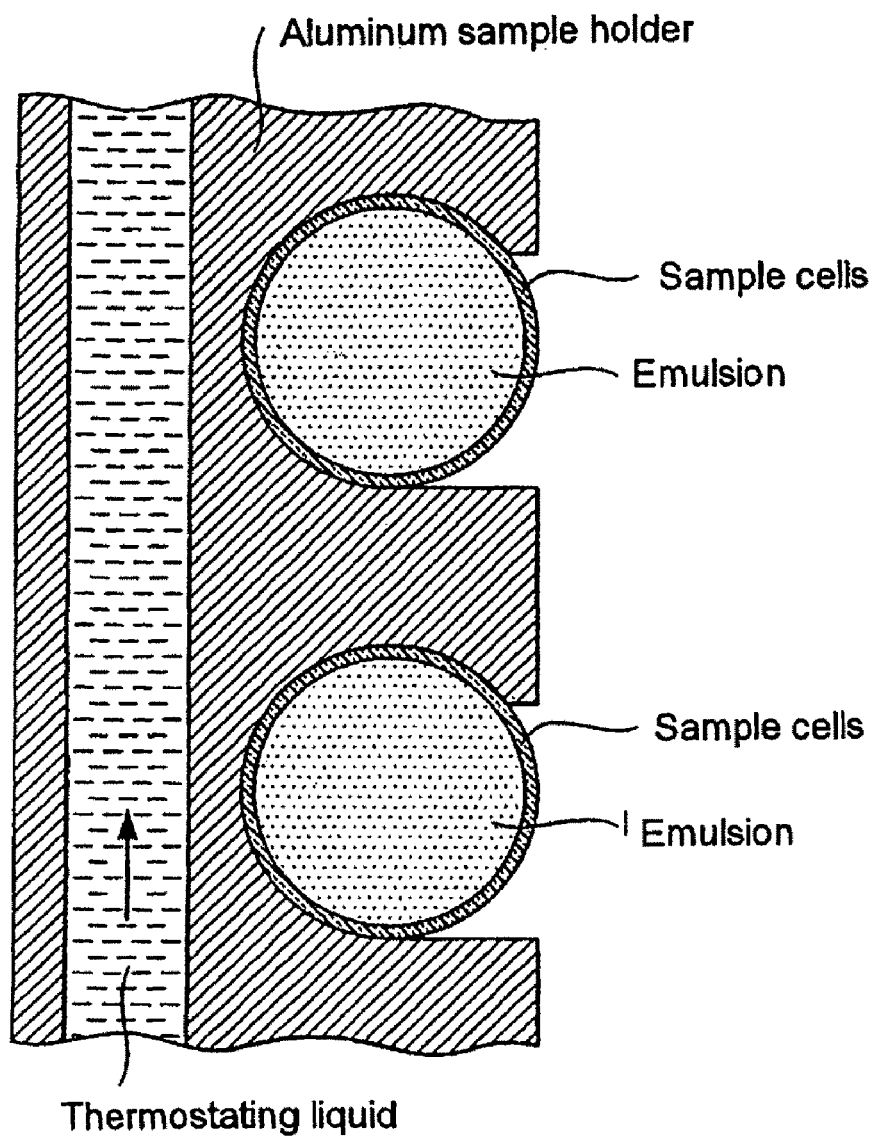
FIG. 1 illustrates a thermostable sample holder useful for assessing emulsion stability.

The invention relates to emulsions of the water-in-oil (W/O) or oil-in-water (O/W) type, containing:
  an oil phase (phase A), containing one substantially water-insoluble component or optionally a plurality of substantially water-insoluble components,
  a water phase (phase B) which may optionally contain further water-soluble components, such as salts or organic compounds, such as alcohols, carboxylic acids or other compounds,
  pyrogenic silica which is arranged at the oil-water interface and is partly silylated in a manner such that the content of non-silylated surface silanol groups on the silica surface is from not more than 95% to not less than 5% of the starting silica, equivalent to from 1.7 to 0.1 SiOH groups per $nm^2$ of silica surface, the dispersion fraction of the surface energy gamma-s-D is from 30 to 80 $mJ/m^2$ and the specific BET surface area has a value of from 30 to 500 $m^2/g$,
  and optionally further substances, such as pigments or preservatives,
the emulsions having a mean particle size of the disperse phase, i.e. a mean drop diameter, measured by means of laser diffraction, of from 0.5 µm to 500 µm, the emulsions having a low viscosity, low viscosity meaning that the emulsions have relative viscosities $\eta_r$ in the range of from 1 to $10^6$, the relative viscosity being defined as the quotient $\eta_{rel}=\eta/\eta_0$ of the measured viscosity of the emulsion $\eta$, measured at 25° C. and a shear rate $D=10\,s^{-1}$, divided by the viscosity of the pure homogeneous phase $\eta_0$,
and the relative viscosity $\eta_{rel}$ of the emulsion obeys the formula $\eta_{rel}=(1-\Phi/0.74)^{-([\eta]\cdot 0.74)}$, $\Phi$ being the phase volume of the disperse phase and $[\eta]$ being a form factor which is in a range of from 2.5 to 100 for the emulsions according to the invention.

It was surprising and by no means to be foreseen by the person skilled in the art that low-viscosity and sedimentation-stable emulsions having a small particle diameter of the disperse phase are obtainable by using sinter-aggregated pyrogenic silica as a particulate emulsifier. This is surprising in that sinter-aggregated pyrogenic silica is usually used as a rheological additive for increasing the viscosity of liquid media.

Here, sinter aggregates are secondary structures according to DIN 53206, which are permanent under shear conditions as usually occur on dispersing fillers in liquid media, such as, for example, solvent-containing or solvent-free adhesives or coating materials, i.e. cannot be divided into their primary particles. This can be demonstrated, for example, from TEM images of hardened silica-binder dispersions which have only aggregate structures but no isolated primary particles.

Particulate systems consisting of sinter aggregates are furthermore characterized in that the hydrodynamic equivalent diameter obtained in the particle size determination by means of quasielastic light scattering is at least a factor of 2 greater than the diameter of the primary particles obtainable computationally according to the formula $a=6/A_{BET} \cdot d$, where $A_{BET}$ is the specific BET surface area measured by means of nitrogen adsorption according to DIN 66131 and d is the density of the primary particles.

Sinter-aggregated systems are furthermore characterized in that the fractal dimension df of the mass is preferably less than 2.7, where the fractal dimension df is defined as mass being proportional to the radius R to the power df. The fractal dimension of the mass can be determined, for example, by means of small angle X-ray or neutron scattering.

The emulsions according to the invention are preferably substantially free of conventional liquid and solid, purely organic surface-active substances which are not particulate at room temperature and the pressure of the ambient atmosphere, such as nonionic, cationic and anionic emulsifiers.

Here, non-particulate emulsifiers means not particles and colloids but molecules and polymers, following the definition of molecules, polymers, colloids and particles as given in "Dispersionen and Emulsionen [Dispersions and emulsions]", G. Lagaly, O. Schulz, R. Zindel, Steinkopff, Darmstadt 1997, ISBN 3-7985-1087-3, page 14. In general, these organic emulsifiers have a size of less than 1 nm, a molar mass of <10,000 g/mol, a carbon content of >50% by weight, determinable by elemental analysis, and a Mohs' hardness of less than 1.

At the same time, the emulsifiers, of which the emulsions according to the invention are preferably substantially free, generally have a solubility of more than 1% by weight in water at 20° C. and the pressure of the ambient atmosphere, i.e. from 900 to 1100 hPa, in homogeneous or in micellar form. The emulsions according to the invention may contain such surface-active substances up to a maximum concentration of less than 0.1 times, preferably less than 0.01 times, particularly preferably less than 0.001 times, in particular less than 0.0001 times, the critical micelle concentration of these surface-active substances in the water phase; this corresponds to a concentration of these surface-active substances, based on the total weight of the emulsion according to the invention, of less than 10% by weight, preferably less than 2% by weight, particularly preferably less than 1% by weight, in particular 0% by weight.

The emulsion according to the invention contains an oil phase (phase A). Phase A contains one substantially water-insoluble component, optionally a plurality of substantially water-insoluble components. Here, substantially water-insoluble means that the solubility of the components in water alone or as a mixture is less than 10 g/100 g of water, preferably less than 1 g/100 g of water, particularly preferably less than 0.1 g/100 g of water, measured at 20° C. and the pressure of the ambient atmosphere, i.e. from 900 to 1100 hPa. In the case of the emulsion according to the invention, the viscosity of phase A, measured at 20° C. and a shear gradient of 10 s$^{-1}$, is from 0.1 to 1,000,000 mPa·s, preferably from 0.1 to 500,000 mPa·s, particularly preferably from 0.2 to 100,000 mPa·s. In the case of the emulsion according to the invention, the phase A can preferably contain a plurality of components. The individual components may be both substances which are liquid at 20° C. and solids, the total mixture of the individual components having the above-mentioned viscosity. Preferably, but not necessarily, a multicomponent phase A is a true solution, i.e. a homogeneous phase in which no further phase interfaces occur.

Examples of substantially water-insoluble components as may be formed by the phase A of an emulsion according to the invention or may be present in it are aliphatic and aromatic hydrocarbons, alcohols, aldehydes, ketones, ethers, esters, amines, carboxylic acids and derivatives thereof, mercaptans, thioethers, oligomeric or polymeric compounds, such as polyolefins, such as polystyrenes, polypropylenes or polyethylenes, saturated or unsaturated polyesters, such as, for example, polycondensates of phthalic acids and 1,2-propanediols or polycocondensates of phthalic acids, 1,2-propanediols and maleic acids, optionally dissolved in reactive diluents, such as styrenes, polyethers, polyepoxides or monomeric or oligomeric precursors thereof, such as alkylene bis-glycidyl ethers, such as

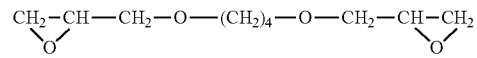

bisphenol A-based diglycidyl ethers, such as

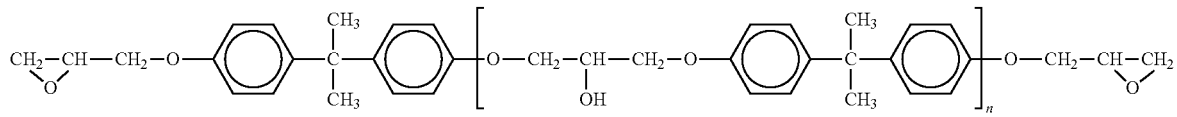

with n preferably from 0 to 10, more preferably from 0 to 5, epoxy novolac resins, such as those of the formula

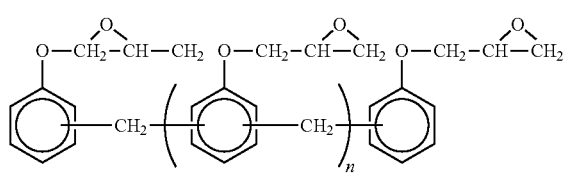

bifunctional epoxy compounds, such as

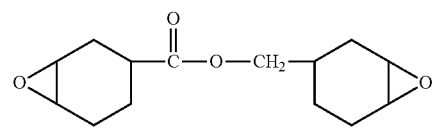 [SMILES: O=C(OCC1CCC2OC2C1)C1CCC2OC2C1]

trifunctional epoxy compounds, such as

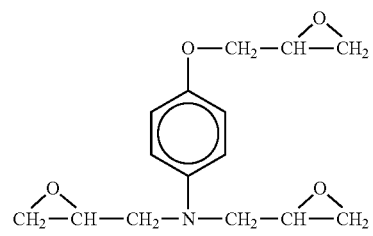

tetrafunctional epoxy compounds, such as

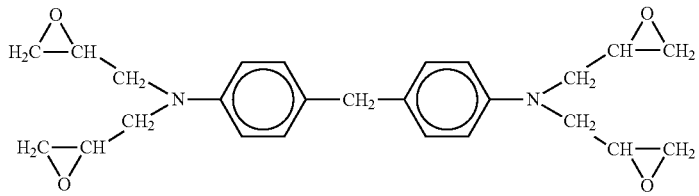

polyurethanes or monomeric or oligomeric precursors thereof, such as, for example, polyetherpolyols, polyacrylatepolyols, polyesterpolyols, polyfunctional isocyanates, such as hexane diisocyanate, toluene diisocyanate, diphenylmethane diisocyanate or isocyanates provided with blocking protective groups, such as hydroxylamines or malonic ester derivatives, complex organic compounds, such as synthetic or natural pharmaceutical or cosmetic active substances, dyes, organo-element compounds, such as organosilicon compounds, such as organo(poly)silanes, organo(poly)siloxanes, organo(poly)silazanes and organo(poly)silcarbanes, or transition metal compounds. Optionally, phase A may contain oil-wettable particles, such as pigments, fillers or rheological additives.

The emulsion according to the invention furthermore contains an aqueous phase (phase B). In addition to water, phase B may contain further components, such as, preferably, acids, bases, salts, water-soluble organic compounds, such as alcohols, carboxylic acids and derivatives thereof, amines or other organic compounds, polymeric or oligomeric compounds, such as polyols or polyamines or polyamidoamines, complex water-soluble organic compounds, such as synthetic or natural pharmaceutical or cosmetic active substances, dyes, organo-element compounds, such as water-soluble organosilicon compounds or water-soluble transition metal compounds. Optionally, phase B may contain water-wettable particles, such as pigments, fillers or rheological additives.

The emulsions according to the invention contain sinter aggregates of suitable pyrogenic silicas, which sinter aggregates are arranged at the oil-water interface. The sinter aggregates used according to the invention are sinter aggregates partly wettable with water, i.e. which are not completely wettable with water and not completely water-unwettable.

The sinter aggregates used according to the invention preferably have a solubility in water, at pH 7.33 and an electrolyte background of 0.11 mol and a temperature of 37° C., of less than 0.1 g/l, more preferably less than 0.05 g/l, at the pressure of the ambient atmosphere, i.e. between 900 and 1100 hPa.

The sinter aggregates used according to the invention preferably have a solubility in water, at pH 7.33 and an electrolyte background of 0.11 mol and a temperature of 37° C., of less than 0.1 g/l, particularly preferably of less than 0.05 g/l, at the pressure of the ambient atmosphere, i.e. between 900 and 1100 hPa.

Preferably, the sinter aggregates used according to the invention have a mean hydrodynamic equivalent diameter $D_h$ of greater than 1 nm, preferably from 1 to 5000 nm, more preferably from 10 to 1000 nm, yet more preferably from 100 to 600 nm, and most preferably from 200 nm to 500 nm, especially from 210 nm to 450 nm, measured in each case preferably by means of dynamic light scattering.

This means that the collision radius $R_c$ of the sinter aggregates which is relevant for the formation of a particle layer in the oil-water interface is greater than 0.8 nm, more preferably from 0.8 to 4000 nm, preferably from 8 to 850 nm, yet more preferably from 80 to 500 nm, and most preferably from 170 nm to 375 nm. The collision radius is the radius of the smallest sphere which just includes all constituents of an aggregate, the collision radius $R_c$ being obtained from the equation $R_c = [R_h^2/0.76 + 2.63 \cdot R_h^2/df]^{0.5}$, as stated in R. de Rooij, A. A. Potanin, D. van den Ende, J. Mellema, J. Chem. Phys. 1993, 99, 9213, the hydrodynamic equivalent radius $R_h$ being obtained from the hydrodynamic equivalent diameter divided by 2 and the fractal dimension of the mass df having a value of 1.8.

The sinter aggregates used according to the invention are furthermore preferably characterized in that, in the particle size determination by means of quasielastic light scattering, the hydrodynamic equivalent diameter is at least a factor of 2, preferably a factor of from 5 to 50, more preferably a factor of from 7 to 25, and most preferably a factor of from 7.5 to 16.5, based in each case on a specific surface area of 100 m$_2$/g (the factor decreases or increases in a correspondingly linear manner in the case of a smaller or larger surface area), greater than the primary particle diameter obtainable computationally according to the formula $a = 6/A_{BET} \cdot d$, $A_{BET}$ being the specific BET surface area measured by means of nitrogen adsorption according to DIN 66131 and d being the density of the primary particles.

The sinter aggregates used according to the invention preferably have a molar mass greater than 10,000 g/mol, more preferably a molar mass of from 50,000 to 50,000,000 g/mol, and most preferably from 100,000 to 10,000,000 g/mol, measured in each case preferably by means of static light scattering.

The sinter aggregates used according to the invention preferably have a specific BET surface area of from 30 to 500 m$^2$/g, more preferably from 80 to 300 m$^2$/g. The BET surface area is measured by known methods, preferably according to German Industrial Standard DIN 66131 and DIN 66132.

The sinter aggregates used according to the invention preferably have a carbon content of less than 50 percent by weight, a Mohs' hardness greater than 1, more preferably greater than 4, and a surface energy gamma of from 30 to 72.5 mJ/m$^2$ at a temperature of 25° C. and the pressure of the ambient atmosphere, i.e. between 900 and 1100 hPa.

The silica sinter aggregates used according to the invention preferably have a dispersion fraction of the surface energy gamma-s-D of from 30 to 80 mJ/m$^2$, more preferably from 35 to 70 mJ/m$^2$, most preferably from 40 to 70 mJ/m$^2$, at a temperature of 25° C. and the pressure of the ambient atmosphere, i.e. between 900 and 1100 hPa. The dispersion fraction of the surface energy gamma-s-D is measured, for example, according to "Inverse Gas Chromatography"–"Characterisation of Polymers and other Materials", 391 ACS Symposium Series, D R Lloyd, Th C Ward, H P Schreiber, Chapter 18, pages 248-261, ACS, Washington D.C., 1989, ISBN 0-8412-1610-X.

The preferred starting silica, from which the silica used in the emulsions according to the invention and partly wettable with water can be prepared, can be prepared in any desired manner known per se, such as, for example, in a flame reaction from halogen-silicon compounds, for example from silicon tetrachloride, or halogen-organosilicon compounds, such as methylchlorosilanes, such as methyltrichlorosilane, or hydrogenchlorosilanes, such as hydrogentrichlorosilane, or other hydrogenmethylchlorosilanes, such as hydrogenmethyldichlorosilane, or alkylchlorosilanes, also as a mixture with hydrocarbons, or any desired sprayable and, preferably, volatilizable mixtures of organosilicon compounds, as mentioned, and hydrocarbons, it being possible for the flame to be a hydrogen-oxygen flame or a carbon monoxide-oxygen flame. The preparation of the silica can be effected alternatively with or without further addition of water, for example in the purification step; preferably, no water is added.

Preferably, partly hydrophobized, more preferably partly silylated, silica sinter aggregates are used as silica sinter aggregates for the preparation of the emulsions according to the invention. Here, partly silylated means that neither is the total silica surface unsilylated nor is the total silica surface silylated.

The degree of coverage τ of the surface of the silica sinter aggregates with silylating agent radicals is preferably from 5 to 95%, more preferably from 10 to 90%, in particular from 15% to 75%, based on the total particle surface.

The coverage with silylating agent can be determined, for example, by means of elemental analysis, such as, for example, via the carbon content, or by determination of the residual content of reactive surface silanol groups of the silica sinter aggregates.

Partial silylation furthermore means that the content of non-silylated surface silanol groups on the silica surface is from not more than 95% to not less than 5%, more preferably from 90 to 10%, in particular from 85 to 25%, of the silanol groups of the starting silica.

This means that the density of the surface silanol groups SiOH is preferably from not less than 0.1 to not more than 1.7, preferably from 0.2 to 1.6, more preferably from 0.45 to 1.55, SiOH per nm² of particle surface.

For a starting silica of 200 m²/g of specific surface area, which can be used for the silylation, this preferably means not less than 0.03 mmol/g of SiOH and not more than 0.57 mmol/g of SiOH, preferably from 0.06 to 0.54 mmol/g of SiOH, more preferably from 0.15 to 0.51 mmol/g of SiOH; for a silica having a smaller or large surface area, this means linearly proportionally more or less surface silanol groups SiOH.

The silicas used according to the invention have a carbon content of from 0.1 to 20% by weight, preferably from 0.1 to 15% by weight, more preferably from 0.1 to 10% by weight.

Processes for the partial hydrophobing or partial silylation of solid particles are already known.

Preferably, the starting silica has a specific BET surface area of from 25 to 500 m²/g. The starting silica preferably has sinter aggregates (definition according to DIN 53206) in the range of diameters from 200 to 1000 nm, the silica having agglomerates (definition according to DIN 53206) which are composed of sinter aggregates and, depending on the external shear load (e.g. measuring conditions), have sizes of from 1 to 500 μm.

The starting silica preferably has a fractal dimension of the surface of preferably less than or equal to 2.3, the fractal dimension of the surface $D_s$ being defined here as: particle surface A is proportional to the particle radius R to the power of $D_s$. Preferably, the starting silica has a density of accessible surface silanol groups SiOH, i.e. accessible to a chemical reaction, of preferably from 1.5 to 2.5 SiOH per nm² of specific surface area, more preferably from 1.6 to 2.0 SiOH per nm².

For the preparation of the silica sinter aggregates used according to the invention, silicas prepared at high temperature (greater than 1000° C.) can be used as starting silicas, pyrogenically prepared silicas being particularly preferred. It is possible to use hydrophilic silicas which are freshly prepared and obtained directly from the burner, have been temporarily stored or are already in commercial packaging.

Uncompacted silicas having tamped or tapped densities of less than 60 g/l, but also compacted silicas having tamped or tapped densities greater than 60 g/l can be used as starting silicas.

Mixtures of different silicas can be used as starting silicas, for example mixtures of silicas of different BET surface area.

For the silylation of silicas, organosilicon compounds, such as, for example,
(i) organosilanes or organosilazanes of the formula

$$R^1{}_d SiY_{4-d} \quad (I)$$

and/or partial hydrolysis products thereof,
where
$R^1$ may be identical or different and is a monovalent, optionally substituted, optionally mono- or polyunsaturated, optionally aromatic hydrocarbon radical having 1 to 24 carbon atoms which may be interrupted by oxygen atoms,
d is 1, 2 or 3 and
Y may be identical or different and is a halogen atom, monovalent Si—N-bonded nitrogen radical to which a further silyl radical may be bonded, —OR², or —OC(O)OR², where R² is a hydrogen atom or a monovalent, optionally substituted, optionally mono- or polyunsaturated hydrocarbon radical which may be interrupted by oxygen atoms,
or
(ii) linear, branched or cyclic organosiloxanes comprising units of the formula

$$R^3{}_e(OR^4)_f SiO_{(4-e-f)/2} \quad (II)$$

where
$R^3$ may be identical or different and has one of the meanings stated above for $R^1$,
$R^4$ may be identical or different and has a meaning stated for $R^3$,
e is 0, 1, 2 or 3 and
f is 0, 1, 2 or 3, with the proviso that the sum e+f is ≦3,
or
mixtures of (i) and (ii)
can preferably be used.

The organosilicon compounds which may be used for the silylation of the silicas may be, for example, mixtures of silanes or silazanes of the formula (I), those comprising methylchlorosilanes on the one hand or alkoxysilanes and optionally disilazanes on the other hand being preferred.

Examples of $R^1$ in formula I are preferably the methyl, octyl, phenyl and vinyl radical, particularly preferably the methyl radical.

Examples of $R^2$ are preferably the methyl, the ethyl, the propyl and the octyl radical, the methyl and the ethyl radical being preferred.

Examples of organosilanes of the formula (I) are alkylchlorosilanes, such as methyltrichlorosilane, dimethyldichlorosilane, trimethylchlorosilane, octylmethyldichlorosilane, octyltrichlorosilane, octadecylmethyldichlorosilane and octadecyltrichloro-silane, methylmethoxysilanes, such as methyltrimethoxysilane, dimethyldimethoxysilane and trimethylmethoxysilane, methylethoxysilanes, such as methyltriethoxysilane, dimethyldiethoxysilane and trimethylethoxysilane, methylacetoxysilanes, such as methyltriacetoxysilane, dimethyldiacetoxysilane and trimethylacetoxysilane, phenylsilanes, such as phenyltrichlorosilane, phenylmethyldichlorosilane, phenyldimethylchlorosilane, phenyltrimethoxysilane, phenylmethyldimethoxysilane, phenyldimethylmethoxysilane, phenyltriethoxysilane, phenylmethyldiethoxysilane and phenyldimethylethoxy-silane, vinylsilanes, such as vinyltrichlorosilane, vinylmethyldichlorosilane, vinyldimethylchlorosilane, vinyltrimethoxysilane, vinylmethyldimethoxysilane, vinyldimethylmethoxysilane, vinyltriethoxysilane, vinylmethyldiethoxysilane and vinyldimethylethoxy-silane, disilazanes, such as hexamethyldisilazane, divinyl-tetramethyldisilazane and bis(3,3-trifluoropropyl)-tetramethyldisilazane, cyclosilazanes, such as octa-methylcyclotetrasilazane, and silanols, such as trimethylsilanol.

Methyltrichlorosilane, dimethyldichlorosilane and trimethylchlorosilane or hexamethyldisilazane are preferred.

Examples of organosiloxanes of the formula (II) are linear or cyclic dialkylsiloxanes having an average number of dialkylsilyloxy units of more than 3. The dialkylsiloxanes are preferably dimethylsiloxanes. Particularly preferred are linear polydimethylsiloxanes having the following terminal groups: trimethylsilyl-oxy, dimethylhydroxysilyloxy, dimethylchlorosilyloxy, methyldichlorosilyloxy, dimethylmethoxysilyloxy, methyldimethoxysilyloxy, dimethylethoxysilyloxy, methyldiethoxysilyloxy, dimethylacetoxysilyloxy, methyldiacetoxysilyloxy and dimethylhydroxysilyloxy groups, in particular having trimethylsilyloxy or dimethylhydroxysilyloxy terminal groups.

Said polydimethylsiloxanes preferably have a viscosity at 25° C. of from 2 to 100 mPa·s.

Further examples of organosiloxanes are silicone resins, in particular those which contain methyl groups as alkyl groups, more preferably those which contain $R^3_3SiO_{1/2}$ and $SiO_{4/2}$ units or those which contain $R^3SiO_{3/2}$ and optionally $R^3_2SiO_{2/2}$ units, $R^3$ having one of the abovementioned meanings.

Said silicone resins comprising units of the formula (II) preferably have a viscosity at 25° C. of from 500 to 5000 $mm^2/s$.

Preferred silicone resins having a viscosity greater than 1000 $mm^2/s$ at 25° C. are those which can be dissolved in a solvent which can be easily handled technically, such as, preferably alcohols such as methanol, ethanol, isopropanol, ethers, such as diethyl ether, tetrahydrofuran, siloxanes, such as hexamethyl-disiloxane, alkanes, such as cyclohexane or n-octane, aromatics, such as toluene or xylene, in a concentration above 10% by weight and with a viscosity of the mixture of less than 1000 $mm^2/s$ at a temperature of 25° C. and the pressure of the ambient atmosphere.

Preferred among the solid organosiloxanes are those which dissolve in a solvent which can be easily handled technically (as defined above) in a concentration greater than 10% by weight and with a viscosity of the mixture of less than 1000 $mm^2/s$ at a temperature of 25° C.

The hydrophobing and silylation, which is preferably carried out for the preparation of the silica sinter aggregates used according to the invention, can be carried out as a batchwise reaction, i.e. by the batch process, or as a continuous reaction, the continuous reaction being preferred.

The hydrophobing and silylation can be realized in one step or in 2 or 3 successive steps. This means that loading (physisorption of the silylating agent) can be effected upstream of the reaction and preferably a purification step can be effected downstream of the reaction. 3 successive steps are preferred: (1) loading—(2) reaction—(3) purification.

The loading temperature is preferably from −30 to 350° C., preferably from 20 to 120° C.

The reaction temperatures preferably range from 0 to 400° C., particularly preferably from 20 to 330° C.

The reaction times are preferably from 1 minute to 24 hours, preferably from 30 minutes to 4 hours.

The reaction pressure is preferably in the region of atmospheric pressure, i.e. between 900 and 1100 hPa.

The purification temperature preferably ranges from 80 to 400° C.

Effective movement and thorough mixing of silica and silylating agent are necessary during steps (1) loading, (2) reaction and purification (3). This is preferably effected by mechanical or gas-borne fluidization. Gas-borne fluidization can be effected by all inert gases which do not lead to secondary reactions, degradation reactions, oxidation processes and flame and explosion phenomena. Here, the superficial gas velocity is from 0.05 to 5 cm/s, particularly preferably from 0.05 to 1 cm/s. Mechanical fluidization can be effected by means of paddle stirrers, anchor stirrers and other suitable stirring members.

In a particularly preferred embodiment, only the amount of gas which is sufficient for maintaining an atmosphere with a low oxygen content, preferably less than 5% by volume, is fed in, and the fluidization is then effected purely mechanically.

The reaction is preferably carried out in an atmosphere which does not lead to oxidation of the silylated silica, i.e. preferably less than 10% by volume of oxygen, particularly preferably less than 2.5% by volume, best results being obtained at less than 1% by volume of oxygen.

Effective introduction of the silylating agent into the silica takes place. If the silylating agents are liquid compounds at the application temperature, effective spraying techniques are preferably used. Spraying in unary nozzles under pressure (from 5 to 20 bar), spraying in binary nozzles under pressure (gas and liquid, from 2 to 20 bar), very fine distribution using atomizers, etc.

The silylating agent is preferably added as a very finely divided aerosol, the aerosol having a settling rate of, preferably, from 0.1 to 20 cm/s and a drop size with an aerodynamic equivalent diameter of from 5 to 25 µm.

Alternatively, protic solvents can preferably be added, such as liquid or vaporizable alcohols or water; typical alcohols are isopropanol, ethanol and methanol. It is also possible to add mixtures of the abovementioned protic solvents. Preferably, no protic solvents are added.

Alternatively, acidic or basic catalysts can preferably be added. These catalysts may have a basic character in the sense of a Lewis base or a Brønsted base, such as ammonia, or acidic character, in the sense of a Lewis acid or a Brønsted acid, such as hydrogen chloride. If catalysts are used, traces are preferred, i.e. less than 1000 ppm. Most preferably, no catalysts are added.

The purification step is characterized by movement, slow movement and slight mixing being preferred.

The purification step is furthermore characterized by increased introduction of gas, corresponding to a superficial gas velocity of from 0.001 to 10 cm/s.

In addition, the purification step may comprise mixing by means of mechanical stirring members. The stirring members are adjusted and moved so that preferably mixing and fluidization but not complete vortexing occur.

Methods from mechanical compaction, such as, for example, press rolls, ball mills, edge mills, screw compactors and briquetters, can be used during the silylation step.

In addition, processes for the deagglomeration of the silica, such as pin-disk mills or apparatuses for milling classification, and/or methods for mechanical compaction of the silica, such as, for example, press rolls, or compaction by sucking out the air or gas content by suitable vacuum methods, or other methods for mechanical compaction, such as, for example, press rolls, ball mills, edge mills, screw compactors and briquetters, can be used before, during or after the silylation step.

The preparation of the silica sinter aggregates according to the invention can also be effected in situ in the preparation of the emulsions according to the invention.

The emulsions according to the invention contain silica sinter aggregates in amounts of, preferably, from 0.1 to 50 parts by weight, particularly preferably from 1 to 15 parts by weight, in particular from 2 to 10 parts by weight, based on 100 parts by weight of total emulsion.

In the case of the emulsions according to the invention, the volume fraction $\Phi_O$ of the oil phase, defined as $\Phi_O$=volume of oil phase/(volume of oil phase+volume of water phase), can preferably be from 0.1 to 0.9, preferably from 0.2 to 0.8, more preferably from 0.3 to 0.7, and in particular from 0.4 to 0.6.

In the case of the emulsions according to the invention, the volume fraction $\Phi_W$ of the water phase, defined as $\Phi_W$=volume of water phase/(volume of oil phase+volume of water phase), can preferably be from 0.1 to 0.9, preferably from 0.2 to 0.8, more preferably from 0.3 to 0.7, and in particular from 0.4 to 0.6.

The emulsions according to the invention are characterized in particular in that the mean particle size of the disperse phase, i.e. the mean drop diameter, measured by means of laser diffraction, for example on a laser diffraction apparatus from Sympatec by the cell measuring technique, is preferably from 0.5 μm to 500 μm, more preferably from 0.7 μm to 100 μm, still more preferably from 0.7 μm to 50 μm and most preferably from 0.7 μm to 10 μm.

The sinter aggregate-stabilized emulsions according to the invention are characterized in particular in that they have a low viscosity. Here, low viscosity means that the emulsions according to the invention have relative viscosities $\eta_r$ in the range of from 1 to $10^6$, preferably from 1 to $5 \cdot 10^5$, more preferably less than $10^5$. The relative viscosity is defined as the quotient $\eta_{rel}=\eta/\eta_0$ of the measured viscosity of emulsion $\eta$, measured at 25° C. using a cone-and-plate system with a measuring gap of 105 μm and a shear rate D=10 s$^{-1}$, divided by the viscosity of the pure homogeneous phase $\eta_0$, measured at 25° C.

The sinter aggregate-stabilized emulsions according to the invention are furthermore characterized in that the relative viscosity $\eta_{rel}$ of the emulsion obeys the formula $\eta_{rel}=(1-\Phi/0.74)^{-([\eta] \cdot 0.74)}$. Here, $\Phi$ is the phase volume of the disperse phase and $[\eta]$ is a form factor which is in a range of from 2.5 to 100, preferably from 2.5 to 50 and very particularly preferably from 2.5 to 10 for the emulsions according to the invention.

The particle-stabilized emulsions according to the invention are distinguished in particular by the fact that they are substantially stable to separation of the disperse phase, i.e. substantially stable to creaming or sedimentation of the disperse phase. Here, substantially stable to separation means that the volume of the phase depleted in dispersion is less than 10% of the total volume, preferably less than 5% of the total volume, more preferably less than 1% of the total volume.

The emulsion stability was investigated by means of the stability analyzer described below.

The invention furthermore relates to a stability analyzer, said stability analyzer having a flat-bed scanner having a sample holder for holding measuring cells perpendicularly to the scanner lamp, a tilted mirror which deflects the light of the scanner laterally onto the measuring cells, and an evaluation apparatus for evaluating the light received.

Round glass cells having an external diameter of 12.5 mm and a height of 50 mm are arranged in a row on a flat-bed scanner (e.g. HPScanJet 3300C from Hewlett-Packard). The cells are secured by a thermostatable sample holder (FIG. 1) to prevent them from slipping.

Figure 2:
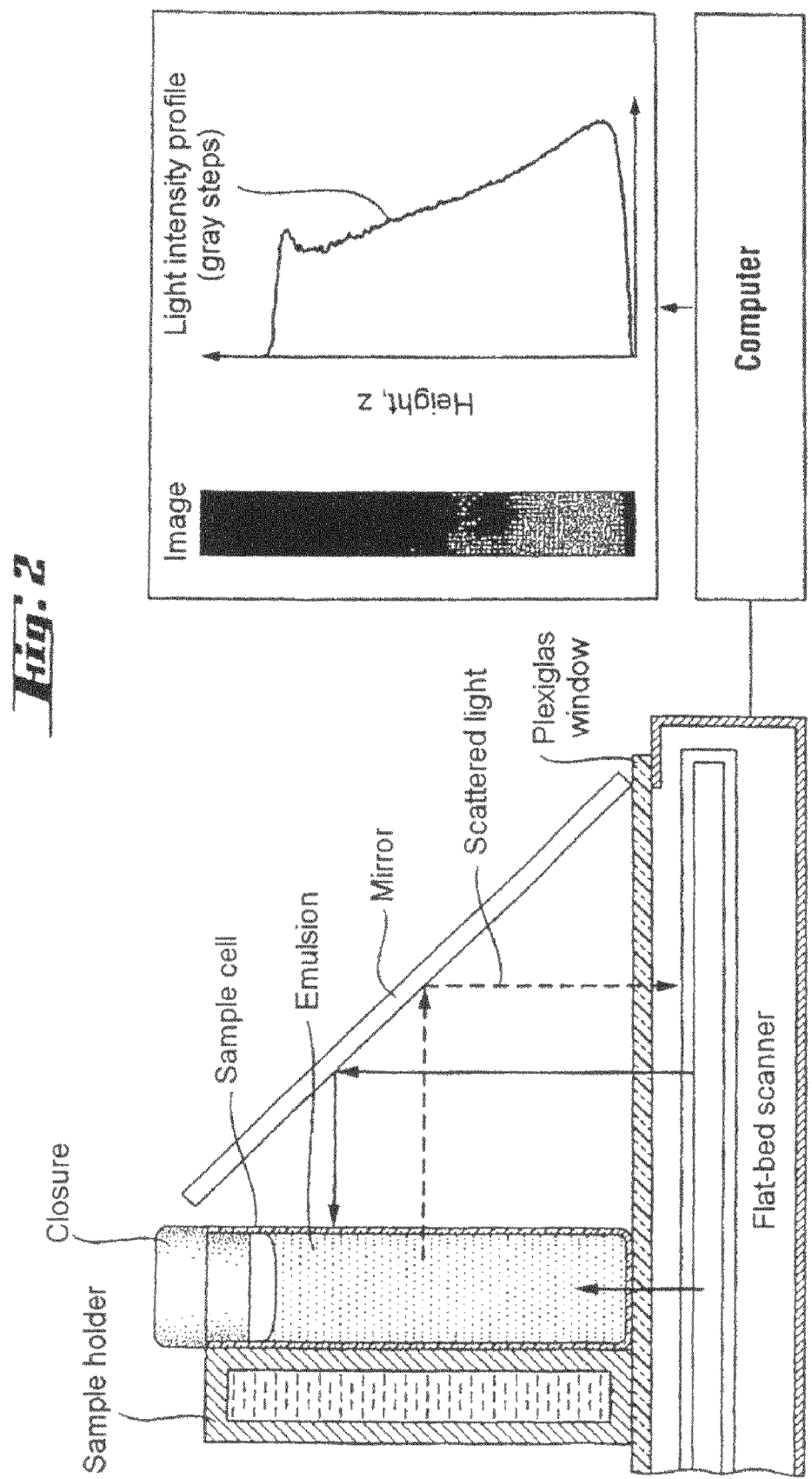
FIG. 2 illustrates the use of a flat bed scanner with the sample holder of FIG. 1, and a gray scale plot obtained therefrom.

The samples are aligned on the flat-bed scanner parallel to the longitudinal side of the scanner, i.e. perpendicular to the scanner lamp (see FIG. 2).

Each sample holder contains up to 12 samples, and all together 24 samples per measuring process can be investigated simultaneously. Image generation will be effected by a procedure in which the light of the scanner lamp is deflected laterally onto the measuring cells by a tilted mirror. At the same time, the emulsion is transilluminated through the bottom of the cell (thick arrows in FIG. 2). The scattered light produced by the emulsion (dashed arrows in FIG. 2) is then deflected back by the mirror to the sensor of the flat-bed scanner. The light path can be adjusted by adjusting screws (not shown for the sake of clarity). For protecting the scanner from contamination and the samples from heat due to the scanner lamp, a 2 mm thick plexiglass screen is also present on the scanner window.

The light received is digitized by the scanner and stored on a computer in the form of, preferably, a bitmap file having 256 gray steps. For determining the gray steps, i.e. the scatter light intensity, at a height h from the bottom of the cell, the light intensities of 60 pixels of a row are averaged according to the formula $$I_{av}(h) = \left(\sum_{i=1}^{60} I\right) / 60.$$

$I_{av}(h)$ corresponds to the gray step at the height h from the bottom of the cell. In the case of a flat-bed scanner with 600 dpi, the total scattered light intensity distribution, as shown, for example in FIG. 2, comprising 980 rows of 60 pixels each is obtained.

The measuring and evaluation process for 24 sample cells takes less than 2 min, i.e. less than 5 s per cell.

Figure 3:
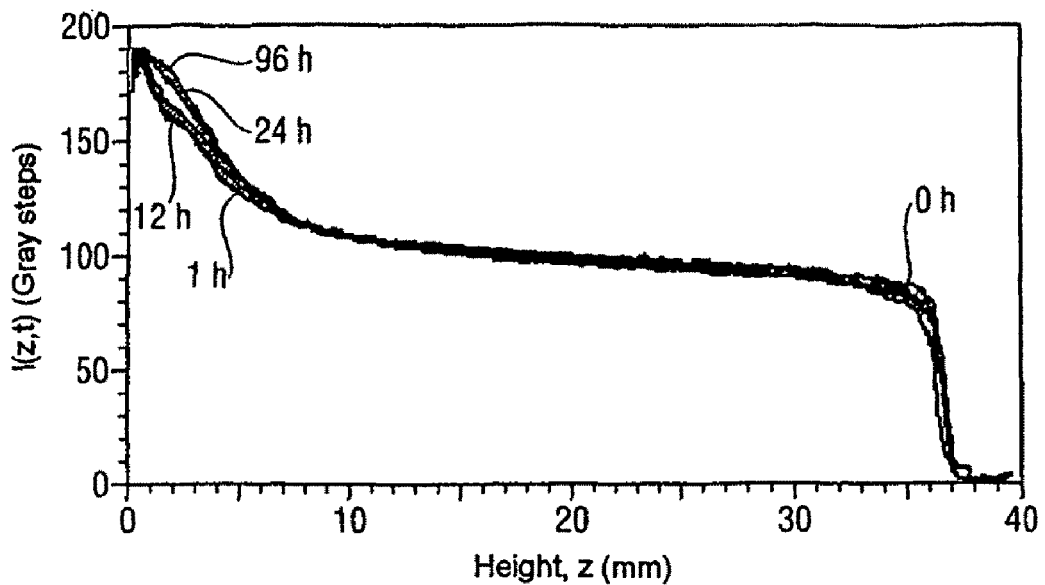
FIGS. 3 and 4 depict plots of scattered light intensity as a function of cell height for an unstable emulsion.
Figure 4:
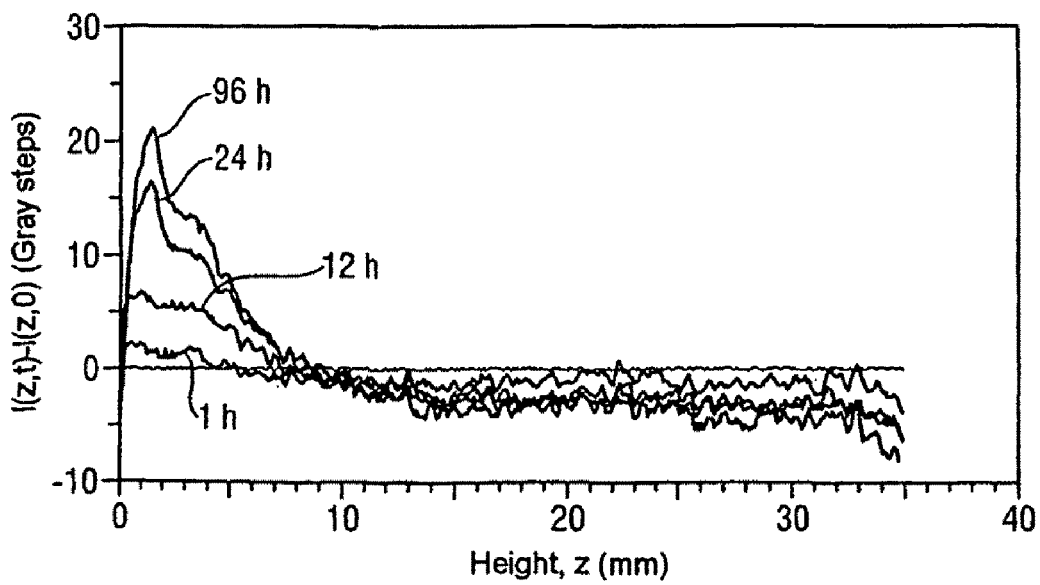

Evaluation is now effected by plotting the measured scattered light intensity as a function of the height measured from the bottom of the cell. Measurements at defined distances are carried for evaluating the stability of an emulsion. A plot of $\Delta I(z,t)=I(z,t)-I(z,0)$, where $I(z,t)$ is the scattered light intensity at the height z at time t and $I(z,0)$ is the scattered light intensity at the height z at the time 0, gives the change in the scattered light intensity with time. A positive change means a higher concentration of scattering particles and therefore indicates separation of the emulsion; analogously, a decrease in the scattered light intensity in a certain volume element as a function of time is a depletion of particles capable of scattering in this element. FIGS. 3 and 4 illustrate this by way of example for an unstable emulsion.

A further subject is a process for the preparation of the emulsions, a highly concentrated finely divided dispersion of the corresponding silica in the liquid which forms the homogenous phase in the emulsion being prepared in a first step, and a highly viscous preemulsion which comprises the total amount of the disperse phase and the highly concentrated finely divided dispersion of the silica, prepared in the first step, in the liquid which forms the homogeneous phase in the emulsion according to the invention being prepared in a second step, the volume of dispersion used being such that the total amount of sinter-aggregated silica required is present, and the remaining homogeneous phase being slowly being metered in a third step.

An emulsification process in which a state of high viscosity, referred to below as "stiff phase", is passed through during emulsification proved to be important for achieving the above-described properties of the emulsions according to the invention.

Specifically, the process for the preparation of the emulsions according to the invention comprises the following individual steps:

Preparation of a highly concentrated finely divided dispersion of the corresponding suitable silica in the liquid which forms the homogeneous phase in the emulsion according to the invention.

Preparation of highly viscous preemulsion consisting of the highly concentrated finely divided dispersion of the corresponding suitable silica in the liquid which forms the homogeneous phase in the emulsion according to the invention, the volume used being such that the total amount of the required sinter-aggregated silica is present, and the total amount of the dispersed phase slow metering in of the remaining homogeneous phase with shearing.

The preparation of the highly concentrated finely disperse dispersion of the corresponding suitable silica in the liquid which forms the homogeneous phase in the emulsion according to the invention can in principle be effected according to the known processes for the preparation of silica dispersions, such as incorporation by means of stirring members with high shear effect, such as high-speed stirrers, high-speed dissolvers, rotor-stator systems, ultrasonic dispersers or ball or bead mills.

The concentration of the silica sinter aggregates in the dispersion is between 1 and 80% by weight, preferably between 10 and 60% by weight, more preferably between 10 and 40% by weight and most preferably between 12 and 30% by weight.

The preparation of the highly viscous preemulsion can be effected in principle according to the known processes for the preparation of emulsions, but it has been found that the processes described below are particularly suitable for obtaining the emulsions according to the invention.

Process 1:
Initially introducing the highly concentrated silica dispersion described above, the initially introduced volume being such that it contains the total amount of silica sinter aggregates required.

Slowly metering in the total volume of disperse phase with continuous homogenization, for example by means of a high-speed stirrer, high-speed dissolver or a rotor-stator system.

Then slowly metering in the desired remaining volume of pure homogeneous phase, optionally with continuous homogenization, for example by means of a high-speed stirrer, high-speed dissolver or a rotor-stator system.

Process 2:
Initially introducing the total volume of disperse phase.
Slowly metering in the highly concentrated silica dispersion described above with continuous homogenization, for example by means of a high-speed stirrer, high-speed dissolver or a rotor-stator system, the volume metered in being such that it contains the total amount of silica sinter aggregates required.

Then slowly metering in the desired remaining volume of pure homogeneous phase, optionally with continuous homogenization, for example by means of a high-speed stirrer, high-speed dissolver or a rotor-stator system.

The processes described can be carried out both in continuous and in batchwise form. The continuous form is preferred.

The temperature of the liquid phase during the emulsification process is between 0° C. and 80° C., preferably between 10° C. and 50° C., more preferably between 20° C. and 40° C.

The emulsification process can be carried out at atmospheric pressure, i.e. at from 900 to 1100 hPa, at elevated pressure, or in vacuo. The process at atmospheric pressure is preferred.

The emulsions according to the invention can be used for all purposes for which emulsions are already used to date. These are in particular water-based coating materials, adhesives and sealants, containing, for example, organosilicon compounds, such as organo(poly)silanes, organo(poly)siloxanes, organo(poly)silazanes and organo(poly)silcarbanes; polyolefins, such as silyl-terminated polyisobutylenes (for example, obtainable under the brand Epion from Kaneka Corp., Japan); saturated or unsaturated polyesters, such as, for example, polycondensates of phthalic acids and 1,2-propanediols or polycocondensates of phthalic acids, 1,2-propanediols and maleic acids, optionally dissolved in reactive diluents, such as styrenes; polyurethanes, polyols, such as hydroxyl-containing polyesters, hydroxyl-containing polyethers, methyldimethoxysilylpropyl-terminated polypropylene glycols (for example, obtainable as "MS polymers" from Kaneka Corp., Japan), hydroxyl-containing polyacrylates; polyisocyanates, such as aliphatic and aromatic polyisocyanates, isocyanate-terminated polyurethane prepolymers, prepared by reacting polyols with polyisocyanates in excess, and the silyl-terminated derivatives thereof (for example, obtainable under the name DESMOSEAL® from Bayer AG, Germany); polyurethanes or precursors thereof, such as, for example, polyetherpolyols, poly-acrylatepolyols, polyesterpolyols, polyfunctional iso-cyanates, such as hexane diisocyanate, toluene diiso-cyanate, diphenylmethane diisocyanate or isocyanates provided with blocking protective groups, such as hydroxylamines or malonic ester derivatives; (poly)-epoxy compounds, such as bisphenol A-based epoxides, monomeric, oligomeric and polymeric compounds containing glycidyloxy functions, such as diglycidyl ethers based on bisphenol A, epoxy novolac raw materials and resins, epoxyalkyd resins, epoxy-acrylates, aliphatic epoxides, such as linear alkylene bisglycidyl ethers, and cycloaliphatic glycidyl ethers, such as 3,4-epoxycyclohexyl 3,4-epoxycyclohexanecarboxylates, and aromatic epoxides, such as triglycidyl ethers of p-aminophenol and triglycidyl ethers of methylenedianiline; (poly)amines, such as cyclic and linear amines, such as hexamethylenediamine, aromatic amines, such as 4,4'methylenebis(2,6-diethylaniline), bis(2-aminoalkyl) polyalkylene oxide, such as bis(2-aminopropyl)polypropylene glycol, and Jeffamines, (poly)amidoamines, (poly)mercaptans, (poly)carboxylic acid, (poly)carboxylic anhydrides; acrylates and esters thereof, such as glycidyl acrylates, alkyl acrylates and esters thereof, methacrylates and esters thereof, polysulfide-forming polymers and polysulfides, such as thioplasts (for example, obtainable under the brand Thiokol from Toray Thiokol Co. Ltd.).

Examples of epoxy compounds are alkylene bisglycidyl ethers, such as

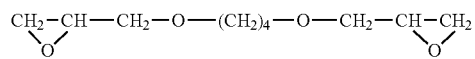

bisphenol A-based diglycidyl ethers, such as

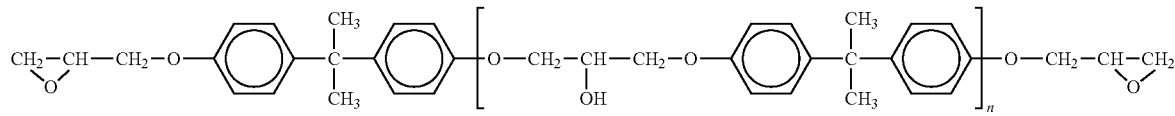

with n preferably from 0 to 10, more preferably from 0 to 5.
Examples of epoxy novolac resins are those of the formula

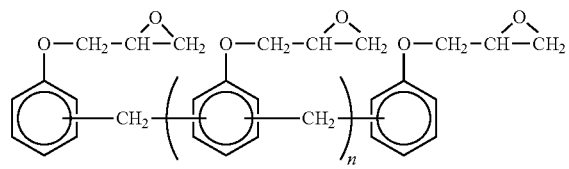

bifunctional epoxy compounds, such as

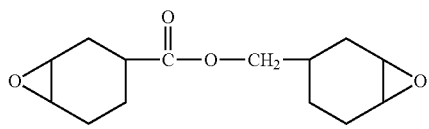 [SMILES: O=C(OCC1CCC2OC2C1)C1CCC2OC2C1]

and trifunctional epoxy compounds, such as

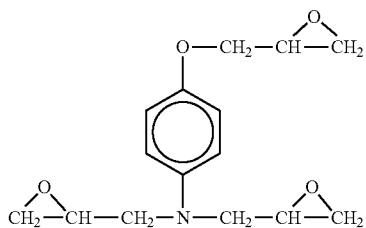

tetrafunctional epoxy compounds, such as

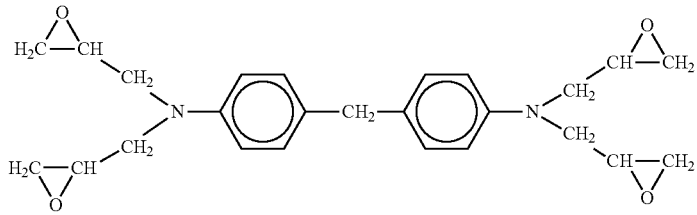

Furthermore, the emulsions according to the invention can be used for cosmetic and pharmaceutical applications, cleaning and cleansing agents or applications for changing the interfacial properties of solid and liquid substrates, such as, for example, water repellents, adhesion promoters, release agents, paper coatings or foam control agents. Furthermore, the emulsions according to the invention can be used for the preparation of w/o/w or o/w/o multiple emulsions, for example as control release systems or for the segregation of reactive substances.

The emulsions according to the invention have the advantage that they are substantially stable to separation, i.e. substantially stable to creaming or sedimentation of the disperse phase.

The emulsions according to the invention furthermore have the advantage that they have low shear viscosities and thus permit easy application.

EXAMPLE 1

Preparation of Solid Particles 100 g of a pyrogenic silica having a specific BET surface area, according to DIN 66131 and DIN 66132, of 200 m²/g (obtainable from Wacker-Chemie GmbH, Munich, Germany, under the name Wacker HDK® N20) are fluidized with stirring (at 1000 rpm with a stirring blade diameter of 12.5 cm) and then treated and blanketed for 15 minutes with nitrogen gas, and the nitrogen stream is then switched off again. Thereafter, 2 g of dimethyldichlorosilane are sprayed by means of a binary nozzle as an aerosol into the fluidized silica, at a temperature of about 25° C. and an ambient pressure of about 1013 hPa. After stirring for a further 30 minutes, the silica thus treated is then heated for 2 hours at 300° C. in an oven having a capacity of 100 l, under a gentle stream of 1000 l/h of nitrogen.

A white pulverulent silica having the following properties is obtained:

The silica has limited but not complete wettability with water; this is evident from the fact that only 16% by weight of the silica can be incorporated into water using Ultraturrax to give a flowable material stable for one day; however, 24% by weight of the starting silica (HDK® N20), which is completely wettable with water, can be incorporated under the same conditions and at the same viscosity.

Further properties of the silica are summarized in Table 1

TABLE 1

| Property | Silica B1 according to Example 1 |
|---|---|
| BET surface area | 184 m²/g |
| Residual content of non-silylated silica silanol groups | 80% |
| Carbon content % C | 0.5% by weight |

TABLE 1-continued

| Property | Silica B1 according to Example 1 |
|---|---|
| Methanol number | 0 |
| Contact angle THETA Method 1 against water and air | 84° |
| Contact angle THETA Method 2 against water and air | 80° |
| Surface energy GAMMA | 69 mJ/m$^2$ |
| Dispersion fraction of surface energy GAMMA-s-D | 65 mJ/m$^2$ |

Specific BET surface area, measured to DIN 66131 and DIN 66132

Residual content of non-silylated silica silanol groups, obtained as quotient (a) of the amount of silica silanol group of the silica prepared as mentioned above, divided by the amount of silica silanol groups of the untreated starting silica (Wacker HDK® N20); the amount of silica silanol groups is determined by acid-base titration (analogous to G. W. Sears, Anal. Chem. 28 (12), (1950), 1981). Method: acid-base titration of the silica suspended in water/methanol=50:50; titration in the range above the pH range of the isoelectric point and below the pH range of the dissolution of the silica; untreated silica comprising 100% of SiOH (silica surface silanol groups): SiOH-phil=1.8 SiOH/nm$^2$; silylated silica: SiOH-silyl; residual content of non-silylated silica silanol groups; % SiOH =SiOH-silyl/SiOH-phil·100% carbon content % C determined by means of elemental analysis for carbon; combustion of the sample at above 1000° C. in an O$_2$ stream, detection and quantification of the resulting CO$_2$ using IR; LECO 244 apparatus Methanol number, measured as follows: test (% by volume of MeOH in water) of the wettability with water-methanol mixtures=methanol number (MN): shaking of an equal volume of silica with an equal volume of water-methanol mixture; start with 0% of methanol; if no wetting occurs, silica floats; a mixture with a 5% by volume higher MeOH content should be used; on wetting, silica sinks; portion of MeOH (%) in water gives the methanol number (MN)

Contact angle THETA method 1 against water, measured as follows: the contact angle of the particles is obtained by careful preparation, by conventional methods, of a pellet of the silica and subsequent determination of the contact angle against water, in this case a deposited water drop comprising bidistilled water in air, by digital image evaluation.

The contact angle θ defines the ratio of the surface tensions and surface energies γ of liquids (l) and solids (s) in a gas space (g) as follows:

$\cos \theta = (\gamma(sl) - \gamma(sg))/\gamma(lg)$

The surface energy (mJ/m$^2$) of a solid is dimensionally identical to the surface tension of a liquid (mN/m), since [J]=[N·m].

Contact angle THETA method 2 against water, measured as by means of an imbibition method using the Lucas-Washburn equation, based on the aspiration of a known and defined liquid, with a known surface tension, into a defined specimen, in this case a slightly compacted pellet of the silica having an open porosity greater than 0.25 and a pore radius r. The aspiration rate dh/dt and the height of the aspirated liquid column h are calculated from the mass absorption m of liquid by the particle heap as a function of the time t, and the viscosity of the aspirated liquid η and the surface tension γ of the aspirated liquid make it possible, in the case of a known particle radius r, to calculate the cosine value of θ ($\cos(\theta)$) and hence the contact angle θ of the liquid against the particle surface by means of the equation according to *Lucas-Washburn* (Washburn, E. W., Phys. Rev. 17, 273 (1921) and R. Lucas, Kolloid s. 23, 15 (1918)); following J. Schoelkopf et al., J. Colloid. Interf. Sci. 227, 119-131 (2000).

Methanol-water mixtures having mixing ratios (volume of methanol to volume of water) are 0:100, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, 100:0 are used as liquid having a known surface tension.

$dh/dt = r \cdot \gamma \cdot \cos(\theta)/(4 \cdot \eta)$ and $h^2 = r \cdot \gamma \cdot t \cdot \cos(\theta)/(2 \cdot \eta)$ $t = A \cdot m^2$      Washburn equation with t: time
m: mass of the aspirated liquid $$A = \frac{\eta}{\{C \cdot \rho^2 \cdot \gamma \cdot \cos\theta\}}$$

η: viscosity of the liquid
ρ: density of the liquid
γ: surface tension of the liquid
θ: contact angle of liquid-powder
C: factor, only dependent on the geometrical properties of the powder and of the sample tube An illustration of the method of measurement is to be found in FIG. 5.

The surface energy GAMMA can be determined for particles as critical surface energy GAMMA-crit. by means of a Zisman plot which, as shown in FIG. 6, plots the respective contact angle THETA of the silica against a defined liquid, as determined above by the imbibition method, against the contact angle of the respective liquids.

However, for particles such as pyrogenic silica which form agglomerates having bulk densities $d_{SD} \ll 1$ g/ml but consist of primary particles having material densities $d_{MD} > 1$ g/ml, shaking into liquids of different surface tension can be used as a method: when wetting does not take place, the particle agglomerates float; in case of wetting, the air in the agglomerates is displaced and the particle agglomerates sink.

By using different liquids and different surface tension, the surface tension of a liquid at which the particle agglomerates sink can be exactly determined; this gives the critical surface energy $\gamma_{crit}$ as a measure of the surface energy γ of the particles.

The method can also be simplified in such a way that the surface tension of water (72.5 mN/m) is reduced by addition of methanol, ethanol or isopropanol.

Typically, water can be initially introduced, a certain amount of particle agglomerates laid (floating) on the water surface and the alcohol then added by titration, with stirring. The water-to-alcohol ratio on sinking of the particle agglomerates is noted and the surface tension is determined for this water:alcohol ratio exactly in a separate experiment using standard methods (ring detachment method, Wilhelmy method).

More effectively, and as carried out here, defined mixtures of water with methanol are prepared, and the surface tensions of these mixtures are then determined. In a separate experiment, these water:methanol mixtures are covered with a layer of defined amounts of particle agglomerates (for example in a volume ratio of 1:1) and shaken under defined conditions (for example, gentle shaking with the hand or using a tumble mixer for about 1 minute).

The water:methanol mixture in which the particle agglomerates just fail to sink and the water:methanol mixture having a higher methanol content, in which the particle agglomerates just sink, are determined. The surface tension of the latter methanol:water mixture gives the critical surface energy $\gamma_{crit}$ as a measure of the surface energy $\gamma$ of the particles, as shown in Table 1.

The dispersion fraction of the surface energy gamma-s-D is determined by using inverse gas chromatography and alkanes as probes, in line with "Inverse Gaschromatographie [Inverse gas chromatography]"—"Characterisation of Polymers and other Materials", 391 ACS Symposium Series, D R Lloyd, Th C Ward, H P Schreiber, Chapter 18, pages 248-261, ACS, Washington D.C. 1989, ISBN 0-8412-1610-X.

16 g of the partly hydrophobic silica described above are predispersed in 84 g of demineralized water in a 500 ml stainless steel beaker by means of a dissolver having a toothed disk. The highly viscous but still flowable material obtained is pumped through an ultrasonic cell at a flow rate of 10 ml per minute and with an amplitude power of 300 watt. The analytical data of the dispersion thus obtained are summarized in Table 2.

TABLE 2

| Property | Aqueous Dispersion from Example 1 |
|---|---|
| Solids content | 16.1% |
| pH | 5.3 |
| Mean diameter Sinter aggregates | 302 nm |
| Viscosity | 240 mPas |

Solids content of the dispersion determined by the following method: 10 g of aqueous dispersion are mixed with the same amount of ethanol in a porcelain dish and evaporated to constant weight in an $N_2$-flushed drying oven at 150° C. The mass $m_s$ of the dry residue gives the solids content according to solids content/%=$m_s$·100/10 g.

pH measured by means of a pH combination electrode
mean diameter of the sinter aggregates measured by means of photocorrelation spectroscopy by the following method: 4 samples of the dispersion to be measured which have a silica content of 1% by weight, 0.75% by weight, 0.5% by weight and 0.25% by weight are prepared in demineralized water by stirring in the appropriate amount of starting dispersion by means of a magnetic stirrer. The samples are measured in a PCS apparatus Coulter N4 Plus from Coulter at detection angles of 30.1°, 62.6° and 90°. The mean diameter of the sinter aggregates is obtained by extrapolating the angle-dependent measured values obtained to a silica content of 0% by weight and then averaging over the three measured angles.

Viscosity of the dispersion was determined using a rheometer MCR 600 from Haake with a cone-and-plate sensor system (105 μm measuring gap) at 25° C. and a shear rate D=10 $s^{-1}$.

78 g of the above-described silica dispersion having a solids content of 16% by weight are initially introduced into a 500 ml stainless steel beaker. 150 g of a polydimethylsiloxane having a viscosity of 100 mPas (obtainable under the name "AK100" from Wacker-Chemie GmbH, Munich, Germany) are slowly metered in over a period of 15 min with stirring at 10,000 rpm using an Ultraturrax and while cooling with water. The temperature of the mixture should not exceed 60° C. 86 g of demineralized water are then slowly added over a period of 15 min, likewise at 10,000 rpm, to this now highly viscous stable material. The temperature of the mixture should not exceed 60° C. A low-viscosity white O/W emulsion results, the analytical data of which are summarized in Table 3.

EXAMPLE 2

78 g of silica dispersion according to Example 1 are initially introduced into a 500 ml stainless steel beaker. While stirring at 10,000 rpm using an Ultraturrax and while cooling with water, 150 g of methyl nonanoate are metered in slowly over a period of min. The temperature of the mixture should not exceed 60° C. 86 g of demineralized water are then slowly added over a period of 15 min, likewise at 10,000 rpm, to this now highly viscous stable material. The temperature of the mixture should not exceed 60° C. A low-viscosity white O/W emulsion results, the analytical data of which are summarized in Table 3.

EXAMPLE 3

150 g of an OH-terminated polydimethylsiloxane having a viscosity of 1000 mPas (obtainable under the name "OH 1000" from Wacker-Chemie GmbH, Munich, Germany) are initially introduced into a 500 ml stainless steel beaker. While stirring at 10,000 rpm using an Ultraturrax and while cooling with water, 78 g of silica dispersion according to Example 1 are slowly metered in over a period of 15 min. The temperature of the mixture should not exceed 60° C. 86 g of demineralized water are then slowly added over a period of 15 min, likewise at 10,000 rpm, to this now highly viscous stable material. The temperature of the mixture should not exceed 60° C. A low-viscosity white O/W emulsion results, the analytical data of which are summarized in Table 3.

EXAMPLE 4

78 g of silica dispersion according to Example 1 are initially introduced into a 500 ml stainless steel beaker. While stirring at 10,000 rpm using an Ultraturrax and while cooling with water, 150 g of a solution of 125 g of the epoxy resin Epikote 828 in 25 g of xylene are metered in slowly over a period of min. The temperature of the mixture should not exceed 60° C. 86 g of demineralized water are then slowly added over a period of 15 min, likewise at 10,000 rpm, to this now highly viscous stable material. The temperature of the mixture should not exceed 60° C. A low-viscosity white O/W emulsion results, the analytical data of which are summarized in Table 3.

EXAMPLE 5

5 g of partly hydrophobic silica having a degree of hydrophobing of 50% and a carbon content of 1.1% (obtainable under the name "Wacker HDK H20" from Wacker-Chemie GmbH, Munich, Germany) are stirred into 85 g of isododecane in a 500 ml stainless steel beaker by means of a dissolver having a toothed disk, and dispersing is then effected for 10 min at 10,000 rpm. 120 g of demineralized water are slowly metered over a period of 15 min into this now highly viscous dispersion with stirring at 10,000 rpm using an Ultraturrax and while cooling with water. The temperature of the mixture should not exceed 60° C. 95 g of isododecane are then slowly added over a period of 15 min to the resulting stable material at 1000 rpm. The temperature of the mixture should not exceed 60° C. A low-viscosity white W/O emulsion results, the analytical data of which are summarized in Table 3.

EXAMPLE 6

94 g of the silica dispersion from Example 1, having a solids content of 16% by weight, are initially introduced into a 500 ml stainless steel beaker. 180 g of a polydimethylsiloxane having a viscosity of 100 mPas (obtainable under the name "AK100" from Wacker-Chemie GmbH, Munich, Germany) are slowly metered in over a period of 15 min with stirring at 10,000 rpm using an Ultraturrax and while cooling with water. The temperature of the mixture should not exceed 60° C. 41 g of demineralized water are then slowly added over a period of 15 min, likewise at 10,000 rpm, to this now highly viscous stable material. The temperature of the mixture should not exceed 60° C. A low-viscosity white O/W emulsion results, the analytical data of which are summarized in Table 3.

TABLE 3

| | Example 1 | Example 2 | Example 3 | Example 4 | Example 5 | Example 6 |
|---|---|---|---|---|---|---|
| Type | O/W | O/W | O/W | O/W | W/O | O/W |
| $\eta_{rel}$ | 148 | 127 | 320 | 273 | 150 | 27 |
| [η] | 6.0 | 5.8 | 6.9 | 6.7 | 8.7 | 5.7 |
| $d_{50}/\mu m$ | 7.67 | 4.76 | 10.9 | 3.82 | 3.50 | 6.42 |
| $\Phi_W/\Phi_O$ | 50/50 | 50/50 | 50/50 | 50/50 | 40/60 | 40/60 |
| $V_{sep}/\%$ | <1 | <1 | <1 | <1 | about 5 | about 8 |

The invention claimed is:

1. A process for the preparation of a product emulsion comprising an oil phase (A) and an aqueous phase (B) comprising preparing a highly concentrated finely divided dispersion of pyrogenic silica in a portion of a liquid which forms a homogeneous phase in the emulsion in a first step to form a highly viscous dispersion; in a second step, adding the total amount of a disperse phase to the highly concentrated finely divided dispersion of pyrogenic silica prepared in the first step, the volume of dispersion used being such that the total amount of pyrogenic silica required in the product emulsion is present; and metering in the remaining portion of the homogeneous phase in a third step, wherein pyrogenic silica is present at an oil-water interface of the oil phase (A) and the aqueous phase (B), the pyrogenic silica being partly silylated such that the content of non-silylated surface silanol groups on the silica surface is from not more than 95% to not less than 5% of the silanol groups of the starting silica, or from 1.7 to 0.1 SiOH groups per $nm^2$ of silica surface, the dispersion fraction of the surface energy gamma-s-D being from 30 to 80 $mJ/m^2$ and the specific BET surface area being from 30 to 500 $m^2/g$, and wherein the emulsions have a mean particle size of the dispersed phase of from 0.5 μm to 500 μm and a relative viscosity $\eta_r$ in the range of from 1 to $10^6$, the relative viscosity being defined as the quotient $\eta/\eta_0$ where η is the measured viscosity of the emulsion at 25° C. and a shear rate $D=10\ s^{-1}$, and $\eta_0$ is the viscosity of the pure homogeneous phase, and wherein the relative viscosity of the emulsion obeys the formula $\eta_{rel}=(1-\Phi/0.74)^{-([\eta]\cdot 0.74)}$, Φ being the volume of the dispersed phase and [η] being a form factor from 2.5 to 10.

2. The process of claim 1, wherein the continuous phase is an aqueous phase, and the emulsion is an oil-in-water emulsion.

3. The process of claim 1, wherein the product emulsion shows no creaming, sedimentation, or phase separation.

4. The process of claim 1, wherein the continuous phase is an aqueous phase and the dispersed phase comprises an epoxy resin.

5. The process of claim 1, wherein at least one phase comprises an organopolysiloxane.

6. The process of claim 1, wherein the density of surface silanol groups on the partly silylated pyrogenic silica is from 0.45 to 1.55 $SiOH/nm^2$ of surface area.

7. The process of claim 1, wherein no organic emulsifiers are present.

8. The process of claim 1, wherein the dispersed phase has a mean diameter of from 0.7 μm to 100 μm.

* * * * *